US010285779B2

(12) United States Patent
Juillerat et al.

(10) Patent No.: US 10,285,779 B2
(45) Date of Patent: May 14, 2019

(54) DENTAL AND/OR SURGICAL INSTRUMENT WITH A CARTRIDGE, AND A CORRESPONDING CARTRIDGE

(71) Applicant: Bien-Air Holding SA, Bienne (CH)

(72) Inventors: Sébastien Juillerat, Moutier (CH); Marc Schenk, Thielle-Wavre (CH)

(73) Assignee: BIEN-AIR HOLDING SA, Bienne (CH)

( * ) Notice: Subject to any disclaimer, the term of this patent is extended or adjusted under 35 U.S.C. 154(b) by 0 days.

(21) Appl. No.: 15/552,628

(22) PCT Filed: Mar. 7, 2016

(86) PCT No.: PCT/EP2016/054796
§ 371 (c)(1),
(2) Date: Aug. 22, 2017

(87) PCT Pub. No.: WO2016/142342
PCT Pub. Date: Sep. 15, 2016

(65) Prior Publication Data
US 2018/0021105 A1    Jan. 25, 2018

(30) Foreign Application Priority Data
Mar. 7, 2015   (CH) ..................................... 00315/15

(51) Int. Cl.
*A61C 1/14*    (2006.01)
*A61C 1/18*    (2006.01)
(Continued)

(52) U.S. Cl.
CPC .............. *A61C 1/141* (2013.01); *A61C 1/181* (2013.01); *F16C 35/077* (2013.01);
(Continued)

(58) Field of Classification Search
CPC .............. A61C 1/10; A61C 1/12; A61C 1/141
See application file for complete search history.

(56) References Cited

U.S. PATENT DOCUMENTS 3,418,715 A * 12/1968 Ellis .......................... A61C 1/05
433/126
5,252,065 A * 10/1993 Nakanishi .............. A61C 1/052
433/115
(Continued)

FOREIGN PATENT DOCUMENTS

EP    0527473 A1    2/1993
EP    0724867 A2    8/1996
(Continued)

OTHER PUBLICATIONS

International Search Report and Written Opinion issued in application No. PCT/EP2016/1054796 dated May 20, 2016; 11 pages.
(Continued)

*Primary Examiner* — Ralph A Lewis
(74) *Attorney, Agent, or Firm* — Pearne & Gordon LLP

(57) ABSTRACT

The present invention relates to a dental and/or surgical instrument (1) comprising a motor that drives a tool by way of a tool holder (24, 25, 27) situated in the head of the dental and/or surgical instrument (1), the tool holder (24, 25, 27) being supported in the head of the dental and/or surgical instrument (1) by at least a first ball bearing (21) and a second ball bearing (22), in which the first ball bearing (21) and the second ball bearing (22) are positioned in a cartridge (10) which is inserted into the head of the dental and/or surgical instrument (1), and in which the cartridge (10) comprises a single bore (80) for the mounting and guiding of both the first ball bearing (21) and the second ball bearing (22). The present invention additionally relates to a cartridge (10) to be inserted into the head of such a dental and/or surgical instrument.

15 Claims, 3 Drawing Sheets

(51) Int. Cl.
*F16C 35/077* (2006.01)
*F16C 19/54* (2006.01)
*A61B 17/072* (2006.01)

(52) U.S. Cl.
CPC ..... *A61B 2017/07271* (2013.01); *A61C 1/145* (2013.01); *F16C 19/547* (2013.01); *F16C 2316/13* (2013.01)

(56) References Cited

U.S. PATENT DOCUMENTS

| | | | | |
|---|---|---|---|---|
| 5,692,903 | A | * | 12/1997 | Nakanishi ............... A61C 1/181 433/115 |
| 7,645,138 | B2 | * | 1/2010 | Boinot ................... A61C 1/141 433/128 |
| 2004/0014005 | A1 | * | 1/2004 | Kuhn ................... A61B 17/162 433/127 |
| 2011/0183286 | A1 | * | 7/2011 | Maitre ............... A61B 17/1622 433/82 |

FOREIGN PATENT DOCUMENTS

| | | |
|---|---|---|
| EP | 1378207 A1 | 1/2004 |
| JP | H0838509 A | 2/1996 |

OTHER PUBLICATIONS

English Translation of International Search Report and Written Opinion issued in application No. PCT/EP2016/054796 dated May 20, 2016; 9 pages.

\* cited by examiner

DENTAL AND/OR SURGICAL INSTRUMENT WITH A CARTRIDGE, AND A CORRESPONDING CARTRIDGE

TECHNICAL FIELD OF THE INVENTION

This invention relates to the field of medical instruments, more particularly dental and/or surgical instruments. More specifically, the present application relates to an improvement in the design of the dental and/or surgical instrument.

In the context of this application, the word "instrument" is used as a generic term designating any working tool of a practitioner, in particular a dentist or a surgeon. Likewise the word "motor" designates in a universal way any device able to create a mechanical movement (in particular a rotating, linear, oscillating, ultrasound movement, etc.), the expression "handpiece" designates in an overall way the device which transmits or which transforms such a mechanical movement, and the word "head" designates the portion of the handpiece constituted by the elements of transmission of the movement at a predefined angle, the guiding elements, and the elements of clamping of the tool.

STATE OF THE ART

Dental and/or surgical instruments are already known comprising handpieces of "turbine" type (with drive by air) or of "contra-angle" type (with a drive by motor and by gearing). In the two cases, the handpieces comprise essentially a system of clamping (and of driving) of the tool which is generally mounted on ball bearings.

As the clamping systems of the tool turn at very high speed, the mechanical precision of the positioning of these systems of clamping of the tool is of essential importance for safety, quality, instrument performance and convenience of the practitioner and comfort of the patient.

The design of the current systems on the market is characterized in that the ball bearing guide diameters are not constituted by a same bore (cylinder) and/or are constituted by an increased mounting complexity for the preloading of the bearings. Consequently, the current systems have the following deficiencies:

- The geometric errors (in particular in the alignment and in the concentricity) contribute toward reducing the dynamic eccentricity of the tool and toward increasing the vibratory phenomena;
- The ball bearings are generally preloaded with the aid of a spring element in order to eliminate the axial play of the tool. Consequently, an error of misalignment will cause an inhomogeneous distribution of the force of preloading of the bearings and accelerate their deterioration;
- For the handpieces of "contra-angle" type, the quality of meshing between the driving and driven gears is essential to guarantee a level of vibro-acoustic quality and ensure a better output for the transmission of forces;
- The systems in which the ball bearing guide bores are machined directly in the head of the handpiece are extremely sensitive to resistance from shocks. A shock on the side of the head of the handpiece can in particular deform locally the material of the head and eliminate the radial play of the bearing. Consequently, it can cause the complete deterioration of the bearing;
- The operational impact involves the number of very precise pieces to be machined and the complexity of assembly; and When the after-sales service is organized so as to operate at a plurality of sites (as is often the case), the replacement of the worn pieces (e.g. ball bearings) requires special tools and a training of technicians for each site.

An example of a document illustrating the solutions known to date and presenting the aforementioned deficiencies is EP 0 527 473 where a large geometric error can occur with respect to the alignment and the concentricity of the ball bearings. In the document EP 1 378 207, the two ball bearings are guided on two different bores, thus creating a risk of faulty concentricity, and having a rather complex mechanism of preloading of the ball bearings with respect to the number of components, the kinematics of mounting, the qualification of personnel and the special tools. Lastly, DE 43 24 493 also presents a rather complex mechanism of preloading of the ball bearings with respect to the number of components, the kinematics of mounting, the qualification of personnel and the special tools, as well as a great susceptibility to shocks.

SUMMARY OF INVENTION

It is thus an object of the present invention to propose a new dental and/or surgical instrument which does not have these deficiencies of the instruments known until today. Very specifically, an object of the present invention is to propose a dental and/or surgical instrument making it possible to reduce maximally the geometrical errors, to improve the distribution of the force of preloading of the bearings and the quality of meshing of the bearings, to provide superior shock resistance, to reduce the number of precise pieces to be machined and then mounted, and lastly to improve the flexibility as regards after-sales service.

To this end, the present invention consists essentially in pre-mounting the element of the head in a "cartridge" (or in a "capsule"), the geometry of the cartridge being conceived in such a way as to optimize the positioning of the shafts of transmission of movement and of alignment of the elements for guiding and clamping of the tool. At the same time, a cartridge according to the present invention can also be easily replaced without resorting to special tools or special methods.

More specifically, the present invention is described in the independent claims, the dependent claims and the description making available the preferred embodiments.

According to a first aspect of the present invention, it relates to a dental and/or surgical instrument comprising a motor driving a tool by way of a tool holder situated in the head of the dental and/or surgical instrument, the tool holder being supported in the head of the dental and/or surgical instrument by at least one first ball bearing and one second ball bearing, in which the first ball bearing and the second ball bearing are positioned in a cartridge which is inserted into the head of the dental and/or surgical instrument, the cartridge comprising a single bore for the mounting and guiding of both the first ball bearing and the second ball bearing.

A single bore for mounting and guiding the two ball bearings supporting the rotary part make it possible to minimize any error in positioning of the bearings and any problem lying in these errors, as will be shown in the following.

According to a second aspect of the present invention, it relates to a cartridge which can be inserted into the head of a dental and/or surgical instrument according to the invention and which comprises a cartridge case with an inner bore and a lateral opening, and a subassembly with a rotor, the first ball bearing, the second ball bearing, as well as a tool holder.

Since it contains all the "active" elements of the head of the instrument, such a cartridge allows a simple replacement.

BRIEF DESCRIPTION OF THE DRAWINGS

The present invention will be better understood from reading the description which will follow, given by way of example and making reference to the drawings in which:

FIG. 2 with the sub

DETAILED DESCRIPTION OF THE INVENTION

Figure 1:
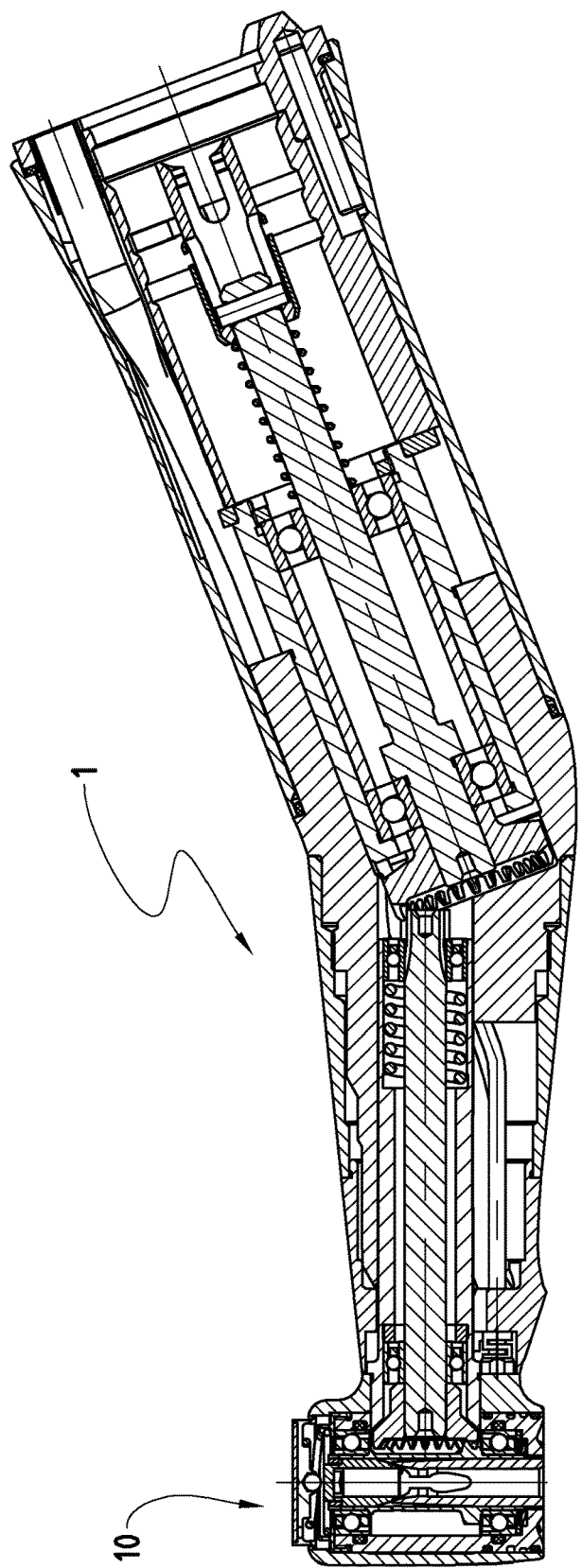
FIG. 1 is a schematic sectional view of a dental and/or surgical instrument according to one embodiment of the present invention.
Figures 2A, 2B, 2C, 2D, 2E:
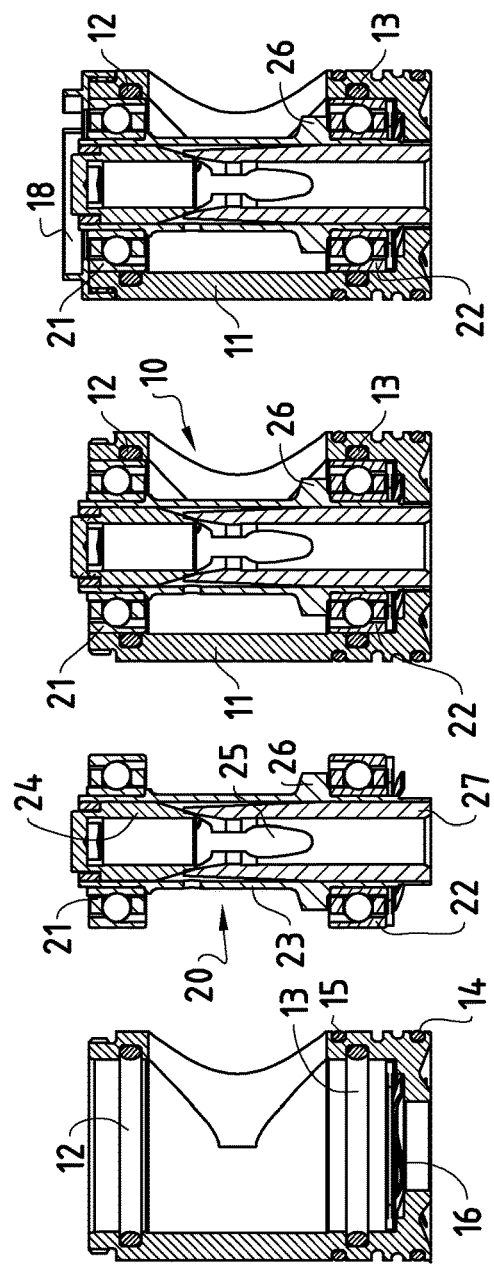
-figures 2A to 2E is a schematic view with a sequence for mounting of a cartridge in the sense of the present invention.
Figure 3:
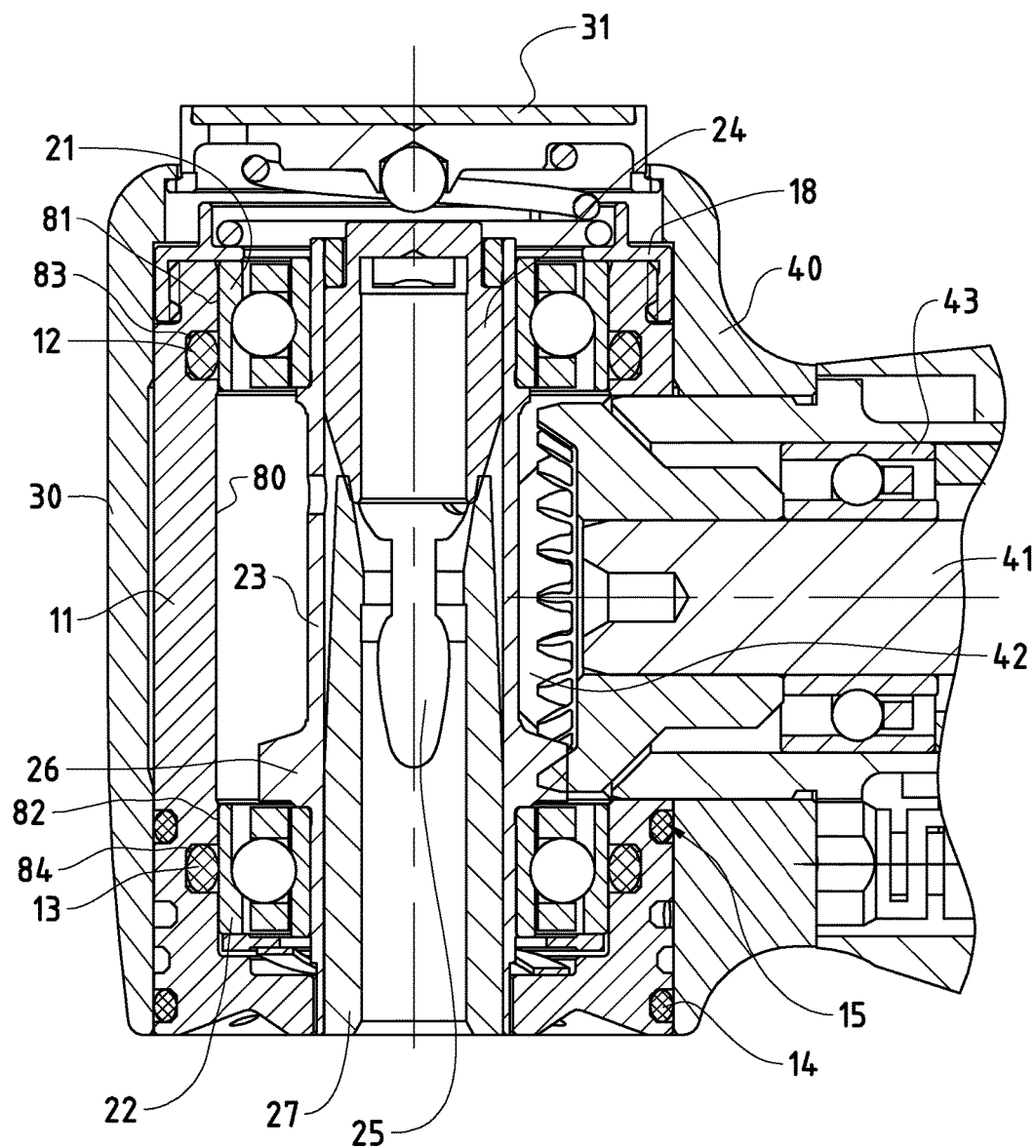
FIG. 3 is a view in section of the head of a dental and/or surgical instrument according to one embodiment of the present invention.

A dental and/or surgical instrument 1 according to one embodiment of the present invention is represented in a schematic way in FIG. 1 and a detail of its structure in FIGS. 2 and 3. Concerned in this example is in particular a "contra-angle" rotary dental and/or surgical instrument, thus an instrument used to bear and drive a dental drill which is then used to get rid of dental tissue softened by caries. This dental instrument 1 comprises in particular a cartridge 10 according to one embodiment of the present invention which will be described in more detail later on. Of course the present invention likewise relates to surgical instruments having the same structure.

An important object of the present invention is to provide a dental and/or surgical instrument in which the geometric error is greatly reduced with respect to existing solutions. In fact, for an optimal functioning and life of the bearings which bear the system of clamping and guiding of the tool (in particular the drill), these bearings must be mounted in such a way that the error of misalignment/faulty concentricity relating to both is as small as possible.

To this end, the present invention proposes to mount and guide the two bearings in a same bore (that is to say in a cylinder), which results in a minimization of the geometric error and other advantages cited below. In the contrary case, each bearing surface or supplementary part can double this relative error.

To arrive at such a solution, the present invention proposes to create this cylinder for mounting and guiding of the ball bearings in a cartridge case called a diffuser and for mounting of the elements for transmission of movement, as well as the elements for guiding and clamping of the tool in this cartridge case. Then, the cartridge case with the mounted elements is sealed and secured before being inserted in the head of the dental and/or surgical instrument.

FIG. 2 with the sub-FIGS. 2A to 2E shows the sequence of mounting of the cartridge according to one embodiment of the present invention.

First a cartridge case 11 is provided as illustrated in FIG. 2A. This cartridge case 11 contains a cylindrical bore 80 on the inside as well as a lateral opening (illustrated by an arrow) which serves to connect the rotor 23 of the cartridge 10 to the driving shaft 41 of the dental and/or surgical instrument 1 (illustrated in FIG. 3). This cylindrical bore 80 serves to mount and guide both the first ball bearing and the second ball bearing, which will be described later.

The bore 80 with the bearing surfaces 81, 82 for guiding of the bearings as well as the grooves 83, 84 which accommodate the damping joints 12, 13 (cf. FIG. 2B) is machined in this cartridge case 11 during a same operation. Consequently, the concentricity error between the two bearings after their mounting is minimized and the compression of the damping joints 12, 13 on their bearings is homogeneous. In the next step, illustrated in FIG. 2B, the damping joints 12, 13 are mounted in the grooves 83, 84 provided for this purpose. Also, a spring for preloading of the bearings 16 is likewise mounted in the cartridge case 11.

The subassembly 20 with a rotor 23 is mounted in parallel, as can be seen in FIG. 2C. This subassembly 20 comprises the two ball bearings 21, 22, as well as the elements for clamping and guiding of the tool (or a tool holder) 24, 25, 27. An outer toothing (or gear) 26 is provided on the rotor 23. This outer toothing 26 meshes with the corresponding toothing 42 of the driving shaft 41 in order to drive in rotation (cf. FIG. 3) this subassembly 20, and thus likewise the tool, when the dental and/or surgical instrument 1 is in operation. This toothing 26 can form an integral part of the rotor 23, but it can also be achieved as a separate piece and forced onto the rotor 23.

The assembled subassembly 20 is mounted in the cartridge case 11 with the pre-mounted damping joints 12, 13 to create the cartridge 10. At the end of this assembly, the cartridge 10 is locked with the aid of a nut 18.

FIG. 3 shows the head of the dental and/or surgical instrument 1 in the assembled state. It can be seen that the cartridge 10 is inserted into the free space created by the wall 30 of the head, then blocked in the head by a standard blocking mechanism 31. It can also be seen in FIG. 3 that the toothing (the gear) 42 of the driving shaft 41 (which is driven by a motor which has not been represented) meshes with the toothing 26 of the cartridge 10 in order to drive in rotation the elements for clamping and guiding of the tool 24, 25, 27 supported by the ball bearings 21, 22. This driving shaft 41 is likewise supported by the ball bearings, a single one of which (reference numeral 43) is visible in FIG. 3.

In addition to this transmission of drive energy, the end of the driving shaft 41 also serves for positioning and locking of the cartridge 10. In effect, and as is visible in FIG. 3, the end of the driving shaft 41 comes to insert itself into the lateral opening (illustrated by an arrow in FIG. 2A) and can thus block the cartridge 10 in the correct position.

In addition to the improvement of the geometry and the reduction of the corresponding error, the dental and/or surgical instrument 1 according to the present invention also has an improvement with respect to the preloading of bearings. In fact, this point is intimately connected with the geometric error mentioned above. If the two ball bearings 21, 22 are not concentric, the force applied for the preloading is not going to be distributed uniformly on the components of each bearing 21, 22. Instead, this force is going to be divided into components which can create undesired constraints accelerating dynamically the deterioration of each bearing 21, 22.

Moreover, and thanks to the locking in place of the cartridge 10 by the end of the driving shaft 41, the quality of meshing is also improved in a dental and/or surgical instrument 1 according to the present invention. In effect, the perpendicularity of the two transmission shafts 41, 23 is also connected with the precision obtained with the machining of the cartridge case (or of the diffuser) 11. The precision of this piece will consequently influence directly the relative positioning between the two transmission shafts 41, 23 and thus improve the quality of the meshing. Of course it is also conceivable to provide a dental and/or surgical instrument 1 in which the transmission shafts 41, 23 are not perpendicular, but inclined, one with respect to the other, at a predetermined angle, notably with the aim to improve the ergonomics of the instrument 1 and/or to respond to anatomical needs.

Another advantage of the dental and/or surgical instrument 1 according to the present invention is the improvement of the resistance to shocks. In the case of a drop or fall, the contact zone of the instrument 1 is very often its distal end. In the dental and/or surgical instrument 1 according to the present invention, the force of the shock is going to be absorbed first of all by the material of the head (that is to say by the outer casing) 30, then by the material of the cartridge 10 itself (thus the wall 11). The achieved solution thus makes it possible to obtain a multilayered effect thanks to the various rigidities of the materials and thus to reduce the propagation of deformations able to destroy the ball bearings 21, 22.

Also, the present invention proposes a rationalization with respect to the number of parts making up the dental and/or surgical instrument 1. In addition, the main advantages are the following:

The quality of guiding of the bearings 21, 22 and of perpendicularity of the transmission shafts 41, 23 resides in the precision of machining of the cartridge case (of the diffuser) 11. Consequently, the overall quality of the mechanism lies in a component able to be machined on standard machining equipment;

The cartridge case (the diffuser) 11 can result in optimization with respect to design, materials and implementation of this component;

The locking of the cartridge 10 by means of a nut 21 allows subassemblies, able to be stored, to be put together for assembly. The preloading is thus arranged just one time;

During assembly, the cartridge 10 is very easily aligned (axially and angularly) by means of the precision bore of the diffuser 11 and the outer diameter of the subassembly of the driving shaft 23. The quality of meshing is thus immediately guaranteed without going through a supplementary operation of adjustment (or review) of the relative positioning between the driving gear 42 and the driven gear 26.

Lastly, the assembly of the cartridge 10 remains an operation of high added value with respect to the function of preloading. However, the advantage of being able to lock the cartridge 10 in its assembled state makes it possible to stock these cartridges and then deliver them as subassemblies for the after-sales service. The after-sales service technician can then simply remove the defective cartridge 10 then replace it very quickly with the aid of minimum tooling.

In the preceding, the invention has been described first in general terms and then in the form of an explanation of practical embodiments. Of course the invention is not limited to the description these modes of implementation; it goes without saying that numerous variations and modifications can be made without going beyond the scope of the invention which is defined by the content of the claims.

The invention claimed is:

1. Dental and/or surgical instrument comprising:
   a motor for driving a tool by way of a tool holder situated in a head of the dental and/or surgical instrument,
   a driving shaft to be driven by the motor, and a rotor for driving the tool in rotation via operative connection to the driving shaft,
   the tool holder being supported in the head of the dental and/or surgical instrument by at least a first ball bearing and a second ball bearing,
   in which the first ball bearing and the second ball bearing are positioned entirely within a cartridge which is removably inserted into the head of the dental and/or surgical instrument,
   wherein the cartridge comprises a single bore for the mounting and guiding of both the first ball bearing and the second ball bearing,
   the single bore having a first bearing surface for guiding the first ball bearing and a second bearing surface for guiding the second ball bearing,
   said first bearing surface and said second bearing surface have the same diameter,
   the cartridge further comprising a lateral opening configured to receive the driving shaft therethrough to facilitate the operative connection between the driving shaft and the rotor.

2. Dental and/or surgical instrument according to claim 1, wherein the single bore is a single cylindrical bore.

3. Dental and/or surgical instrument according to claim 1, wherein the cartridge comprises at least one first groove and one second groove, the first groove serving to accommodate a first damping joint and the second groove serving to accommodate a second damping joint.

4. Dental and/or surgical instrument according to claim 3, wherein the first groove and the second groove, as well as the first bearing surface for guiding of the first ball bearing and the second bearing surface for guiding of the second ball bearing are machined during a same operation.

5. Dental and/or surgical instrument according to claim 1, wherein the cartridge is locked by a nut.

6. Dental and/or surgical instrument according to claim 1, wherein the cartridge is positioned and locked in the head of the dental and/or surgical instrument by means of an end of the driving shaft.

7. Dental and/or surgical instrument according to claim 1, wherein a central axis of the driving shaft is perpendicular to a shaft of the rotor.

8. Dental and/or surgical instrument according to claim 1, wherein an outer casing of the dental and/or surgical instrument is made of a material different from the material of the cartridge.

9. Dental and/or surgical instrument according to claim 1, said cartridge being axially and angularly aligned within the head of said instrument by means of the bore and a matching outer diameter of a subassembly that includes the rotor, said cartridge being locked in place by an end of the driving shaft.

10. Cartridge to be removably inserted in a head of a dental and/or surgical instrument, comprising:
    a cartridge case with an inner bore having a first bearing surface, a second bearing surface, and a lateral opening, said first and second bearing surfaces having the same diameter, and
    a subassembly with a rotor, a first ball bearing positioned entirely with the cartridge and mounted and guided by the first bearing surface of the inner bore, a second ball bearing positioned entirely with the cartridge and mounted and guided by the second bearing surface of the inner bore, and a tool holder supported by at least the first ball bearing and the second ball bearing, wherein the lateral opening of the cartridge case is configured to receive a driving shaft of the dental and/or surgical instrument to facilitate operative connection between said driving shaft and the rotor for driving the tool holder in rotation.

11. Cartridge according to claim 10, wherein the inner bore is a single cylindrical bore.

12. Cartridge according to claim 10, wherein the cartridge case comprises at least one first groove and one second groove, the first groove serving to accommodate a first damping joint and the second groove serving to accommodate a second damping joint.

13. Cartridge according to claim 12, wherein the first groove and the second groove, as well as the first bearing surface for guiding of the first ball bearing and the second bearing surface for guiding of the second ball bearing are machined during a same operation.

14. Cartridge according to claim 10, wherein the rotor comprises an outer toothing able to mesh with a corresponding toothing of a driving shaft.

15. Cartridge according to claim 10, said cartridge configured to be axially and angularly aligned within a head of said instrument by means of the bore and a matching outer diameter of the subassembly, said cartridge being locked in place by an end of the driving shaft.

* * * * *